United States Patent
De Pontes et al.

(10) Patent No.: US 8,598,077 B2
(45) Date of Patent: Dec. 3, 2013

(54) **COMPOSITION BASED ON *BACILLUS* SPP. AND CORRELATE GENERA AND THEIR USE IN PEST CONTROL**

(75) Inventors: Rose Gomes Monnerat Solon De Pontes, Brasília (BR); Carlos Marcelo Silveira Soares, Brasília (BR); Colin Berry, Cardiff (GB)

(73) Assignees: Empresa Brasileira de Pesquisa Agropecuaria—EMBRAPA, Brasilia (BR); Bthek Biotechnologia Ltda., Brasilia (BR); University College Cardiff Consultants Limited, Cardiff (GB)

( * ) Notice: Subject to any disclaimer, the term of this patent is extended or adjusted under 35 U.S.C. 154(b) by 1015 days.

(21) Appl. No.: 12/438,289

(22) PCT Filed: Aug. 29, 2007

(86) PCT No.: PCT/BR2007/000217
§ 371 (c)(1),
(2), (4) Date: Jun. 22, 2009

(87) PCT Pub. No.: WO2008/025108
PCT Pub. Date: Mar. 6, 2008

(65) Prior Publication Data
US 2011/0306494 A1    Dec. 15, 2011

(30) Foreign Application Priority Data
Aug. 29, 2006 (BR) .................................. PI0603879

(51) Int. Cl.
*A01N 25/26* (2006.01)
*A01N 63/00* (2006.01)
(52) U.S. Cl.
USPC .......................................... 504/100; 504/117
(58) Field of Classification Search
None
See application file for complete search history.

(56) References Cited

U.S. PATENT DOCUMENTS 6,455,036 B1 * 9/2002 Quimby et al. ............... 424/93.1
2004/0242424 A1 * 12/2004 Rajamannan ................. 504/164

FOREIGN PATENT DOCUMENTS

| CN | 1506455 A | | 6/2004 |
| EP | 1449914 | * | 8/2004 |
| EP | 1449914 A1 | | 8/2004 |
| RU | 2267926 C1 | | 1/2006 |
| WO | WO0154504 | * | 8/2001 |
| WO | 2004/002223 A2 | | 1/2004 |
| WO | WO2004002223 | * | 1/2004 |

OTHER PUBLICATIONS

Perlak et al(Insect Resistant Cotton Plants, Biotechnology, vol. 8, 1990).*
De Castro(Pantas Transgenicas Resistentes A Insectos—Perspectivas E Limitacoes, Pesq. Agropec. Bras, Brasilia, 27, S/N: 319-324, abr. 1992).*
Cho SJ. et al., "Endophytic colonization of balloon flower by antifungal strain *Bacillus* sp. CY22". Biosci Biothechnol Biochem Oct. 2003, 67(10): 2132-8 PMID 14586100.
Arthur I. Aronson et al., "*Bacillus thuringiensis* and Related Insect Pathogens", Microbiological Reviews, 1986, 50(1): 1-24.
Frederick J. Perlak et al., "Insect Resistant Cotton Plants", Biotechnology, 1990, 8: 939-943.
Luiz Antonio Barreto de Castro, "Plantas transgenicas resistentes a insetos-perspectivas e limitacoes", Peaq. agropec. bras., 1992, 27: 319-324.
Daniel Gerbeim Souza Dias et al., "Avaliacao de larvicidas de origem microbiana no controle de traca-das-cruciferas em couve-flor no Distrito Federal", Comunicado Tecnico, 2002, ISSN: 0102-0099, 1-4.
Soo Jeong Cho et al., "Endophytic Colonization of Balloon Flower by Antifungal Strain *Bacillus* sp. CY22", Biosci. Biotechnol. Biochem., 2003, 67(10): 2132-2138.

* cited by examiner

*Primary Examiner* — Alton Pryor
(74) *Attorney, Agent, or Firm* — Sughrue Mion, PLLC

(57) ABSTRACT

The objective of the current invention is the control of agricultural infestations based on alternative methods that are less aggressive to the environment and that are harmless to other invertebrates and to man; for instance biological control using bacterial strains belonging to species of the genera *Bacillus, Brevibacillus* and/or *Paenibacillus*. A first embodiment of the invention refers to compositions based on the systemic utilization of bacterial strains belonging to species of the genera *Bacillus, Brevibacillus* and/or *Paenibacillus* to protect plants by using the composition containing the above referred bacteria in wild-type, conjugated, mutant or transgenic forms and/or the substances produced by them. A second embodiment of the invention refers to a method of bioinsecticide application based on bacteria from the genera *Bacillus, Brevibacillus* and/or *Paenibacillus*. A third embodiment of the invention is related to the bioinsecticide usage of the formulations based on bacteria from the genera *Bacillus, Brevibacillus* and/or *Paenibacillus*.

5 Claims, No Drawings

US 8,598,077 B2

COMPOSITION BASED ON *BACILLUS* SPP. AND CORRELATE GENERA AND THEIR USE IN PEST CONTROL

FIELD OF INVENTION

The current invention refers to a improved biopesticide composition based on *Bacillus, Paenibacillus* and *Brevibacillus* bacterial genera that provide bacterium or substances produced by them in enough quantity to control pest infestations, especially arthropods, nematodes and molluscs, through systemic action in the plant. The invention also deals with the usages to control pests in plants.

BACKGROUND OF THE INVENTION

The extensive cultivation such as soybean, corn, cotton and canola, among others, requires high investment in pesticides due to the quantity of plagues they harbour, especially arthropods, nematodes and molluscs. The damage caused by the different infestations individually may vary from one region to another, and the cost of their control can reach 35% of the production costs.

The utilization of chemical products has been the principal form of control of these infestations (Dias, D. G. S.; Soares, C. M. S. & Monnerat, R. G. Avaliação de larvicidas de Origem Microbiana no Controle de traça-das-cruciferas em Couve-Flor no Distrito Federal. Embrapa Recursos Genéticos e Biotecnologia, Comunicado Técnico no 74, 4 pgs, 2002), which requires huge investment, representing a burden or even making production impracticable in some cases (Castro, L. A. B. Plantas transgênicas resistentes a insetos: Perspectivas e limitações. Pesq. Agropec. Bras. Brasília, 27, S/N: 319-424, 1992). Moreover, these chemical products pollute the environment and can intoxicate the human beings.

In fact, it is evident the importance of simple and more effective forms of biological control in agriculture. The importance of pest control and the increasing public awareness of the direct and indirect effects of the pesticides in the environment and on public health have required new ways to control infestations and insects, which should to be more economical and less harmful to the ecosystem.

In the specific case of pest control, biological alternatives include the utilization of bacteria, fungi, viruses and even in the utilization of substances produced by the insect itself. These agents can be manipulated in order to increase their patogenicicity and to expand their range of action, industrial production or the incorporation of pesticide genes in plant species, leading to the production of transgenic plants (Perlak, F. J.; Deaton, R. W.; Armstrong, T. A.; Fuchs, R. L. Sims, S. R.; Greenplate, J. T. and Fischhoff, D. A. Insect resistant cotton plants. BioTechnology 8:939-963, 1990.).

From the many microbial agents that have pesticidal activity against insects and other invertebrates), we can highlight the bacteria belonging to the *Bacillus, Brevibacillus* and *Paenibacillus* genera. Species of these bacteria show a large geographical distribution and they are specific in controlling pests. One great advantage of their utilization is that they are harmless to man and domestic animals and they have no polluting effect to the environment The pesticide activity of the bacteria of the *Bacillus, Brevibacillus* and *Paenibacillus* genera is due to the production of toxins during the vegetative or sporulation phases of growth and by infection (Aronson, A. I., Beckman, W. y P. Dunn. *Bacillus thuringiensis* and related insect pathogens. Microbiol. Rev. 50, 1-24. 1986). The variability inside each species of these bacteria is very big. Recent records list more than 300 different toxins produced by *B. thuringiensis*. Due to it, laboratories all over the world are searching for strains with new toxins and other pathogenicity features that enable a higher availability of active principles which will be available for use in control strategies. Embrapa has a collection of 2.300 strains of entomopathogenic bacteria including bacteria from the genera *Bacillus, Brevibacillus* and *Paenibacillus*. Among the known strains, some have proven activity against arthropods, nematodes and molluscs.

Recently in the Laboratory of bacteriology of the Biological control Center of Embrapa Genetic Resources and Biotechnology studies were conducted to verify the possible utilization of insecticidal bacteria in a systemic way in plants.

The usage of biological agents to increase productivity and effectiveness in agriculture has been known for a long time. For example, the document U.S. Pat. No. 6,033,659 describes the use of a *Bacillus cereus* strain, named W35, and its mutants that are able to exert biological control through antibiotics and other toxins produced by this bacterium. According to this patent, plants, including seeds, cuttings and full-grown plants, treated with a sufficient quantity of this bacterium and its toxins or antibiotic produced by the bacterium itself, are protected against rotting or wilting of the root. The bacterium or its products are placed around the immediate neighborhood of the plant or the cutting or even by coating the seed with bacterial material.

The document U.S. Pat. No. 6,232,270 describes a composition comprising (a) an active ingredient effective in agriculture and (b) an enhancer containing a bacterial culture of *Bacillus* genus or a soil bacterium in the form of cells, cultures or suspensions, in sufficient quantity to improve the effectiveness of such active ingredient. *Bacillus thuringiensis* is mentioned in the list of enhancers. The enhancer component contains spores, cultures and suspensions of bacteria of the *Bacillus* genus or a soil bacterium. Preferentially, the enhancer component is in the spore form, as long as there is a appropriate adjustment of temperature, PH and salinity. Preferentially, the enhancer is a ATCC 55675 of the *Bacillus cereus* strain, which improves the effect of the growth plant regulator, Mepiquat chloride and of the Atrizine herbicide, that can be used to select the bacterial species, in order to improve other active ingredients such as systemic insecticides and fungicides. Bacteria found among roots of vigorously growing plants are also preferable as enhancer. The enhancer compound containing bacteria can be applied as a treatment or simultaneously with a variety of active ingredients such as herbicides, systemic pesticides and systemic fungicides. It is also mentioned that the foliar application of the local soil bacteria, at the rate of $0.1 \times 10^{10}$ CFU/acre up to $10 \times 10^{10}$ CFU/acre improves the natural mechanisms associated to the plant growth and propagation to a level sufficient for to the active ingredient to show the improved activity over or inside the treated plant.

It is obvious that the purpose of the use of the composition defined in the patent U.S. Pat. No. 6,232,270 is to improve plant growth and vigour and, in consequence, improve its resistance to pests. In that case, the bacterial component (spores, culture or suspensions of bacteria belonging to *Bacillus* genus) is just an improvement of the active component.

In addition, it is important to point out that, after foliar application of an agent to the treatment of plants, losses or the complete removal of the treatment agent can occur. For example, before absorption, bacteria may be washed from leaves as a result of rain and loss of activity can also occur as a result of ultraviolet rays (solar action), especially in the case of bioinseticides based on *Bacillus thuringiensis* (Bt) which requires high concentrations of endotoxins to be effective against the pests.

Thus, to increase productivity and effectiveness in pest control using biological agents, special attention must be paid to the form of application of the biopesticide to the plant and the quantity of bacteria applied to ensure the activity and permanence of the bacterium in association with the plant.

Thus, the studies mentioned above show that is not easy to obtain satisfactory results of plant treatment with *Bacillus thuringiensis* to control infestations of insects and other invertebrates through the inoculation and the susceptibility of the insects fed by these leaves as a result of the action of the bacterium. This success requires a deep knowledge about the interaction between the microorganism and the plant, about the strain utilized and about the pests' susceptibility to the *Bacillus*. This way, the knowledge of the Bt strains diversity, including biological and physicochemical characteristics of the produced endotoxins, is important to obtain appropriate formulations that ensure exposure of the target-pests to sufficient concentrations of lethal toxins for a long period.

SUMMARY OF THE INVENTION

The objective of the current invention is the control of agricultural infestations based on alternative methods that are less aggressive to the environment and that are harmless to other invertebrates and to man; for instance biological control using bacterial strains belonging to species in the genera *Bacillus, Brevibacillus* and/or *Paenibacillus*.

The first embodiment of the invention refers to compositions based on the systemic utilization of bacterial strains belonging to species of the genera *Bacillus, Brevibacillus* and/or *Paenibacillus* to protect plants by using the composition containing the above referred bacteria in wild-type, conjugated, mutant or transgenic forms and/or the substances produced by them, that are fatal to pests in general, in an amount sufficient to maintain an adequate concentration of the toxic or infective factors in the systemic circulation to be effective in protecting the plant and an adequate vehicle or a composition comprising one species of *Bacillus* that produces a toxic-protein- to the pests or the target-insect, optionally in a mixture with an endophytic *Bacillus thuringiensis* against target-insects in a sufficient amount to keep the systemic circulation of the toxic or infective factors effective in protecting the plant and an agriculturally acceptable vehicle.

A second embodiment of the invention is related with a method of bioinsecticide application based on bacteria from the genera *Bacillus, Brevibacillus* and/or *Paenibacillus*.

A third embodiment of the invention is related to the bioinsecticide usage of the formulations based on bacteria from the genera *Bacillus, Brevibacillus* and/or *Paenibacillus*.

DETAILED DESCRIPTION OF THE INVENTION

With the purpose of clarifying the invention more completely and clearly, several definitions of the terms used here are now presented:

"Plant" means organism where the systemic action of the compound (composition) based on bacteria from the genera *Bacillus, Brevibacillus* and/or *Paenibacillus*, will take place including, monocotyledonous, dicotyledonous, transgenic and non-transgenic plants.

"*Bacillus, Brevibacillus* and *Paenibacillus*" mean strains of wild-type, conjugated, mutant or transgenic bacterial strains belonging to the genera *Bacillus, Brevibacillus* and/or *Paenibacillus*, in their different phases of development, spores and/or vegetative cells and/or the lethal substances to pest invertebrates produced by them.

The microorganisms used in the present invention were identified by the following techniques: selection starting from parts of plants to detect the colonization microorganisms selected from the group consisting of the genera *Bacillus, Brevibacillus* and/or *Paenibacillus* endophytic; conjugation of the selected microorganism selected from the group consisting of the genera *Bacillus, Brevibacillus* and/or *Paenibacillus* endophytic with strains of toxic protein producer *Bacillus thuringiensis* to pest-invertebrate or target-invertebrate; transformation of the microorganism selected from the group consisting of the genera *Bacillus, Brevibacillus* and/or *Paenibacillus* etc.

In a first embodiment of the invention, is provided the use of a composition based on the genera *Bacillus, Brevibacillus* and/or *Paenibacillus* for the systemic protection of plants against pests, especially arthropods, nematodes and molluscs. It should be noted that the systemic property of the active principle, the endotoxin concentration, with bio insecticide activity available in the plant and the frequency of the composition application are relevant factors to the plant properties against the pests. This fact was demonstrated by experiments carried out with *Bacillus thuringiensis*.

In a second embodiment of the invention, is provided a method of application of the formulation based on the genera *Bacillus, Brevibacillus* and/or *Paenibacillus* to plants or their parts which one wishes to protect against pests, especially arthropods, nematodes and molluscs.

As mentioned before, some formulations for application on plants with *B. thuringiensis* (Bt) have already been disclosed. Some authors say that the compound formulation can be liquid, emulsion, suspension and solid grains. These authors also say that, in general, the application is made on the leaves and this kind of utilization is subject to climatic action, including for example, solar ultraviolet rays and the dispersion of the formulation by rain or irrigation.

One of the objectives of the invention is to solve such problems, through a composition that act in the plant for a long time and that is effective against pests when said composition is administered to the plant in the form of, powders, grains, pills, capsules, liquids, suspensions, emulsions, seed inoculants and other fast or slow release formulations. It is important to highlight that the satisfactory results obtained by the current invention are possibly associated to the preferential embodiment of the invention, where it was confirmed that a strain from one species belonging to one of the studied genera was able to be absorbed and to circulate inside the plant. To confirm this fact a strain of the *B. thuringiensis kurstaki* was signed with a "green fluorescent protein" gene to express fluorescent protein (gfp—green fluorescent protein). This technique allowed the identification of the *Bacillus* by fluorescence, in different parts of the plant in a systemic form following inoculation. Fluorescent bacteria could also be recovered from the digestive tracts of insects that had fed on the treated plants.

The compositions of the current invention can have liquid form, such as emulsions or suspensions, or solid form, such as powders, pills, capsules, solid grains, aggregated or compound grains (solid active ingredients on inert particles). Additionally, the solid forms can be of slow release to maintain themselves on the parts of the plant in contact with the pests, in a concentration showing satisfactory pesticidal activity.

The appropriate vehicles for the compositions in this current invention can be selected from a wide range of substances. In the case of solid compositions, the vehicle can be selected from the group consisting of, for example, finely divided solids, pellet, wetable powders, and soluble powders or similar. Many organic and inorganic materials can be used as solid vehicles, for example, diatomaceous earth, clay, sand, vermiculite, corn cob, activated charcoal and mineral silicates, or their blends, among others. Among the mineral silicates. the preferred ones to use in the composition of the invention are glist, pirofilite, clays or similar substances.

The compositions according to the invention can also comprise other liquid or solid adjuvants, such as stabilizers, for example, vegetable oils or vegetable oils epoxides (for example, coconut oil, soy or canola oil), antifoaming agents, for example, silicon oil, preservatives, viscosity regulators, binders and/or thickeners, and solar radiation protectors, such as titanium dioxide among others.

The compositions of the invention can also contain fertilizers or other active ingredients, such as growth regulators, insecticides, nematocides, molluscicides, selective herbicides or any other products used during the cultivation cycle.

The compositions can also be in monophasic or biphasic liquid forms to be applied over seeds or inert particles. The seeds and inert particles treated in this way can form aggregates of controlled- or fast-release or a mix of both forms to ensure the appropriate systemic concentration of bacteria from the genera *Bacillus, Brevibacillus* and/or *Paenibacillus*, and the substances produced by them, in the plant for a reasonably long period, to prolong the time between the applications of the composition. In the embodiment comprising liquid composition, solutions, emulsions or dispersions, the vehicle can be an aqueous liquid, an organic compound or a mix of both.

Examples of organic vehicles are aromatic hydrocarbons, such as toluene and xylene, acetone, methanol, isopropionic alcohol, tertiary butyl alcohol, cyclohexane, dioxane, dimethyl formamide, dimethyl sulphoxide, etilen dichloride, N-methyl pirrolidone, among others. The compositions of the current invention confer protection to the plants against pests at equivalent levels to those obtained with pesticides or genetically modified plants and without the disadvantages of the latter ones. Additionally, the preparation costs and the complexity of production are much lower when compared with pesticides obtained or genetic plants transformation.

The compositions of the invention can be used by any known process, involving known stages, such as, mixture, granulation, sprinkling, pulverization, aspersion, pelletization of seeds, in-soil application and in the water pills, tablets, among others.

According to one preferred form of the invention, the method comprises the application of the composition, solid or liquid, in water or in the soil, in the neighbourhood around the plant. The solid composition can be in the form of powder, pill, capsule, grains, and grain compounds having a rapid or prolonged release of the active ingredient(s) or a mix of both forms. More preferentially, the composition is, in part, in the rapid release form and, in part the prolonged release form. The application can be done on the soil surface or below it, in the water or near the roots of the plant.

Another method of application of the composition based on bacteria from the genera *Bacillus, Brevibacillus* and/or *Paenibacillus* of the invention in the solid and/or monophasic or biphasic liquid forms, in the seeds of the plant that one wishes to protect against pests, especially, arthropods, nematodes and molluscs.

The application of the composition to the seeds can be done by any known process, such as, for example, by pelletization, spraying, immersion, impregnation, or any other appropriate technique. Additionally, the seeds can be agglomerated through appropriate binders as Arabic gum and others. After, seed agglomerates are submitted to drying in appropriate conditions to maintain the pesticidal activity of the composition unaltered.

The following examples represent the embodiments of the invention. It is obvious that the modifications that imply the usage of the inventive concept herein described are included in the objective of this invention.

EXAMPLES

1—Recuperation in the Plant, of *B. thuringiensis* Inoculated in the Soil

This experiment had as its objective the verification the parts of the plant colonized by *B. thuringiensis* and its persistence in the cotton plant tissues. This experiment was performed using a *B. thuringiensis kurstaki* strain that is the international standard for Lepidoptera, transformed with the green fluorescent protein gene (gfp) to express a fluorescent protein. As a result, the strain can be differentiated from other *B. thuringiensis* strains.

The toxicity of the transformed strain was compared with the non-transformed strain in bioassays with larvae of *Spodoptera frugiperda*. The mortality data obtained were analyzed through Probits and the lethal concentration to cause 50% of the larva mortality ($LC_{50}$) was determined. The results showed that the $LC_{50}$ of the strains (transformed and non-transformed) are identical (Table 1).

TABLE 1

The $LC_{50}$ values obtained with non-transformed and gfp-transformed Btk strains against *S. frugiperda* larvae.

| strain | $LC_{50}$ (confidence interval) ng/cm$^2$ |
| --- | --- |
| Btk | 28.5 (20.2-41.9) |
| Btk-gfp | 27.4 (20.4-39.5) |

The experiment was performed by the division of the plants in two groups, the first one with only one application of 5 ml de Btk-gfp and the second one with a weekly application of 5 ml of Btk-gfp. The marked strain (Btk-gfp) was grown in NYSM medium in a rotating incubator (200 rpm, 30° C., 48 hours). Next, 120 cotton plants were planted in plastic pots.

Once a week the tissues of 3 plants treated with Btk-gfp and 3 un-treated plants were collected to detect the presence of the marked strain. To do this the plant was submitted to a superficial sterilization and the strains were isolated according to the method described by Monnerat (Monnerat, R. G.; Santos, R.; Banos, P.; Batista, A.; Berry, C. Isolamento e caracterização de estirpes de *Bacillus thuringiensis* endofíticas de algodão. Brasília, D F: Embrapa Recursos Genéticos e Biotecnologia, 2003. 4 p. Embrapa Recursos Genéticos e Biotecnologia. Comunicado Técnico, 98).

The bacterial colonies obtained were analyzed under a fluorescence microscope to verify the presence of fluorescence. The experiment lasted 9 weeks.

The leaves of each cotton plant, collected two days after initial inoculation with Btk-gfp, were given as food to 30 second stage larvae of *S. frugiperda* in order to verify toxicity of the leaves to these insects. These leaves crucible and inoculated in Petri dishes containing solid medium NYSM. After germinating, the bacteria were observed under a fluorescence microscope to verify the fluorescence.

The treatment of 5 ml suspension once a weekly supplied the Btk-gfp recovery in all parts of the plants during the nine-week experiment (Table 2). In the assay with plants that were treated only one time it was possible to detect the Btk-gfp in the autoclaved soil until the 7$^{th}$ week and in the un-autoclaved soil until the 9th week. In the roots, pedicle and leaves the Btk-gfp was detected until the 8th week in either plants cultivated in autoclaved soil or in un-autoclaved soil. In the stem the detection ended earlier, in the 7$^{th}$ week in plants cultivated in both soils.

TABLE 2

Detection of Btk-gfp in different cotton tissues after one application of Btk-gfp (U), after weekly applications of Btk-gfp (S) and without inoculation of Btk-gfp (C).

| weeks | Soil | | | Root | | | Stem | | | Pedicle | | | Leaf | | |
|---|---|---|---|---|---|---|---|---|---|---|---|---|---|---|---|
| | C | U | S | C | U | S | C | U | S | C | U | S | C | U | S |
| 0 | − | − | − | − | − | − | − | − | − | − | − | − | − | − | − |
| 1 | − | + | + | − | + | + | − | + | + | − | + | + | − | + | + |
| 2 | − | + | + | − | + | + | − | + | + | − | + | + | − | + | + |
| 3 | − | + | + | − | + | + | − | + | + | − | + | + | − | + | + |
| 4 | − | + | + | − | + | + | − | + | + | − | + | + | − | + | + |
| 5 | − | + | + | − | + | + | − | + | + | − | + | + | − | + | + |
| 6 | − | + | + | − | + | + | − | + | + | − | + | + | − | + | + |
| 7 | − | + | + | − | + | + | − | + | + | − | + | + | − | + | + |
| 8 | − | − | + | − | + | + | − | − | + | − | + | + | − | + | + |
| 9 | − | − | − | − | + | − | − | − | − | − | + | − | − | − | + |

The presence of Btk-gfp was detected in all insects used in the experiment (Table 3). The percentage of mortality was very heterogeneous during the nine weeks of the experiment. The leaves collected in the single application experiment caused mortality that varied between 15 to 80% in plants cultivated in autoclaved soil. It is important to notice that this mortality was highest between the third and the fifth week and decreased after the fifth week.

The leaves collected in the weekly application experiment were more toxic, killing 85% to 95% of the larvae, showing statistical differences. As for the single treatment, the weekly treatment achieved the maximum mortality between the third and the sixth week. Nevertheless, they continued killing in a level higher than 60% until the end of the ninth week.

TABLE 3

The average percentage mortality of *S. frugiperda* larvae fed on leaves from plants treated with Btk-gfp once (U), weekly (S) and percentage of insects where the Btk-gfp was detected.

| | U | | S | |
|---|---|---|---|---|
| Weeks | Mortality | Fluorescence | Mortality | Fluorescence |
| 0 | 0 | 0 | 0 | 0 |
| 1 | 25 | 100 | 35 | 100 |
| 2 | 45 | 100 | 40 | 100 |
| 3 | 80 | 100 | 85 | 100 |
| 4 | 55 | 100 | 40 | 100 |
| 5 | 80 | 100 | 75 | 100 |
| 6 | 55 | 100 | 85 | 100 |
| 7 | 15 | 100 | 65 | 100 |
| 8 | 25 | 100 | 55 | 100 |
| 9 | 25 | 100 | 60 | 100 |

The results indicated that the Btk-gfp is absorbed by the cotton plant roots and goes to their leaves. The insects fed on treated leaves absorb the Bt, but the dose seems to be insufficient to kill all the insects.

2: Performance Evaluation of Different Forms of *B. thuringiensis* Inoculation

Different forms of the *B. thuringiensis* inoculation were tested: added to seeds, formulated as pills and applied weekly in suspension near to the stem. This experiment was evaluated weekly, three weeks after the planting of the seeds, collecting 3 plants per treatment from the sterile and non-sterile soil. The methodology used for isolation was described by Monnerat et al. (2003, Isolamento e caracterização de estirpes de *Bacillus thuringiensis* endofíticas de algodão. Comunicado técnico 98) and the leaves of each test were given to caterpillars of *S. frugiperda*. In all cases the presence of fluorescence was checked.

A Preparation of the Seeds

Seeds were involved with an inoculant prepared with Btk-gfp. For this purpose it were tested different compositions of inoculants, prepared in different amounts of turf lyophilised Btk-gfp and sugar.

Immediately after being mixed, the inoculant was incubated for 7 days at ambient temperature. The seeds were planted in pots containing sterile and non-sterile soil.

Among the compositions of inoculants tested, the one selected for the assay was the one produced in the following proportions: one hundred grams of turf, in a concentration of 3.5% Btk-gfp and 80 grams of sugar previously added to 50 ml of autoclaved distilled water. One hundred grams of *Gossypium hirsutum* seeds were inoculated. This inoculant composition showed the better features in terms of consistency and bacterial viability than others. Turf is an important substrate for the production of commercial inoculants that has the following characteristics: a high retention of humidity, facility of processing, absence of toxicity to the bacterium, available in large quantity, low cost and good adhesion to the seeds. The sugar was used to give adherence to the ingredients.

The mortality varied between 25 to 80% with seeds inoculated in this way.

B. Pills

The pills were prepared based on the following composition: (a) 3.5% of lyophilized Btk-gfp, (b) 60% starch, (c) 30% modified cellulose, (d) 3.5% of stearate and (e) 3% water. Starch works as a vehicle, modified cellulose works as an adjuvant for slow dispersion and stearate works as a lubricant.

The pills were placed in the plantation lines, near to the seeds in pots containing sterile and non-sterile soil. The mortality varied between 15 and 75% in the treatment with pills.

C. Suspension

Suspensions were prepared containing 3.5% lyophilized Btk-gfp per ml of water. This procedure gave a very homogeneous suspension.

The presence of Btk-gfp was detected in all parts of the plants (Table 4) and in all the insects used in the assay (Table 5), in all treatments, except in the non-treated control. The mortality, however, varied between 15 and 50% in the treatment with suspension.

TABLE 4

Detection of Btk-gfp in different cotton tissues after the treatment with pills (CP), suspension (S), inoculated seeds (I) and control without treatment (C) control. Harvesting performed once a week in cultivated plants in autoclaved soil (A) and non-autoclaved (NA).

| | Soil | | | | | | | | Root | | | | | | | | Stem | | | | | | | |
|---|---|---|---|---|---|---|---|---|---|---|---|---|---|---|---|---|---|---|---|---|---|---|---|---|
| | A | | | | NA | | | | A | | | | NA | | | | A | | | | NA | | | |
| Weeks | C | CP | S | I | C | CP | S | I | C | CP | S | I | C | CP | S | I | C | CP | S | I | C | CP | S | I |
| 0 | − | − | − | − | − | − | − | − | − | − | − | − | − | − | − | − | − | − | − | − | − | − | − | − |
| 3 | − | + | + | + | − | + | + | + | − | + | + | + | − | + | + | + | − | + | + | + | − | + | + | + |
| 4 | − | + | + | + | − | + | + | + | − | + | + | + | − | + | + | + | − | + | + | + | − | + | + | + |
| 5 | − | + | + | + | − | + | + | + | − | + | + | + | − | + | + | + | − | + | + | + | − | + | + | + |
| 6 | − | + | + | + | − | + | + | + | − | + | + | + | − | + | + | + | − | + | + | + | − | + | + | + |
| 7 | − | + | + | + | − | + | + | + | − | + | + | + | − | + | + | + | − | + | + | + | − | + | + | + |
| 8 | − | + | + | + | − | + | + | + | − | + | + | + | − | + | + | + | − | + | + | + | − | + | + | + |

| | Pedicell | | | | | | | | Leaf | | | | | | | |
|---|---|---|---|---|---|---|---|---|---|---|---|---|---|---|---|---|
| | A | | | | NA | | | | A | | | | NA | | | |
| Weeks | C | CP | S | I | C | CP | S | I | C | CP | S | I | C | CP | S | I |
| 0 | − | − | − | − | − | − | − | − | − | − | − | − | − | − | − | − |
| 3 | − | + | + | + | − | + | + | + | − | + | + | + | − | + | + | + |
| 4 | − | + | + | + | − | + | + | + | − | + | + | + | − | + | + | + |
| 5 | − | + | + | + | − | + | + | + | − | + | + | + | − | + | + | + |
| 6 | − | + | + | + | − | + | + | + | − | + | + | + | − | + | + | + |
| 7 | − | + | + | + | − | + | + | + | − | + | + | + | − | + | + | + |
| 8 | − | + | + | + | − | + | + | + | − | + | + | + | − | + | + | + |

TABLE 5

Percentage of mortality to *S. frugiperda* larvae (M) fed on leaves from plants cultivated in autoclaved soil (A) and non-autoclaved (NA) treated with Btk-gfp offered as pills (CP), suspension (S), inoculated seeds (I) and control without treatment (C) and total percentage of insects where the Btk-gfp was detected.(F).

| | CP | | | | S | | | | I | | | | T | | | |
|---|---|---|---|---|---|---|---|---|---|---|---|---|---|---|---|---|
| | A | | NA | | A | | NA | | A | | NA | | A | | NA | |
| eeks | M | F | M | F | M | F | M | F | M | F | M | F | M | F | M | F |
| 0 | 0 | 0 | 0 | 0 | 0 | 0 | 0 | 0 | 0 | 0 | 0 | 0 | 0 | 0 | 0 | 0 |
| 3 | 15 | 100 | 15 | 100 | 15 | 100 | 25 | 100 | 45 | 100 | 30 | 100 | 0 | 0 | 0 | 0 |
| 4 | 25 | 100 | 50 | 100 | 25 | 100 | 15 | 100 | 35 | 100 | 40 | 100 | 0 | 0 | 0 | 0 |
| 5 | 75 | 100 | 30 | 100 | 50 | 100 | 45 | 100 | 80 | 100 | 75 | 100 | 0 | 0 | 0 | 0 |
| 6 | 50 | 100 | 35 | 100 | 25 | 100 | 35 | 100 | 65 | 100 | 60 | 100 | 0 | 0 | 0 | 0 |
| 7 | 35 | 100 | 30 | 100 | 20 | 100 | 15 | 100 | 25 | 100 | 30 | 100 | 0 | 0 | 0 | 0 |
| 8 | 35 | 100 | 35 | 100 | 20 | 100 | 20 | 100 | 20 | 100 | 25 | 100 | 0 | 0 | 0 | 0 |

The observed mortality varied between 15 and 75% in the treatment with pills, between 15 and 50% in the treatment with suspension and between 25 and 80% with inoculated seeds. In a general way the treatment with inoculated seeds was the one which resulted in the greater larval mortality, statistically, though, there have been no significant differences among the treatments. These differences were not significant between the experiments in autoclaved and non-autoclaved soil either. The results obtained have confirmed the possibility of utilization of the composition in different forms of application.

What is claimed:

1. A composition comprising:

*Bacillus thuringiensis;*

60% of vehicle selected from the group diatomaceous earth, clay, sand, vermiculite, corn cob, activated charcoal and mineral silicates, or their blends, starch, glist, pirofilite, and aromatic hydrocarbons;

30% of adjuvant selected from the group vegetable oils, vegetable oils epoxides, antifoaming agents, and solar radiation protectors;

3.5% of lubricant; and

3% of water;

optionally further comprising at least one bacterial strain selected from the group *Brevibacillus* and *Paenibacillus.*

2. A composition comprising:

*Bacillus thuringiensis;*

60% of starch;

30% of modified cellulose;

3.5% of stearate; and

3% of water;

optionally further comprising at least one bacterial strain selected from the group *Brevibacillus* and *Paenibacillus*.

3. A method for systemic pest control wherein said method comprises treating a plant or parts thereof with a composition set forth in claim 1 or 2.

4. The method according to claim 3, wherein said composition is in solid form and is applied on soil surface, in water, in an area around the plant, under soil surface, or near the plant roots.

5. The method according to claim 4, wherein said composition is applied to seeds.

* * * * *